US00PP32962P2

(12) United States Plant Patent
Holtmaat

(10) Patent No.: US PP32,962 P2
(45) Date of Patent: Apr. 6, 2021

(54) ***RUDBECKIA* PLANT NAMED 'RUDTI124'**

(50) Latin Name: *Rudbeckia hirta*
Varietal Denomination: RUDTI124

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 16/873,132

(22) Filed: Feb. 7, 2020

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474, 428
CPC ..... A01H 5/02; A01H 5/00; A01H 6/14
See application file for complete search history.

(56) References Cited

U.S. PATENT DOCUMENTS

PP30,657 P2 * 7/2019 Holtmaat ..... A01H 5/02
Plt./474

OTHER PUBLICATIONS

AB Cultivars *Rudbeckia* 'Tiger', retrieved on Jul. 30, 2020, retrieved from the Internet at https://www.ab-cultivars.com/?portfolio=rudbeckia-tiger-smileyz, one page. (Year: 2020).*

Newey 2019 Catalogue Perennial Plugs and Liners, retrieved on Jul. 27, 2020, retrieved from the Internet at https://www.newey.com/wp-content/uploads/Newey-PPL-Catalogue-2019.pdf, cover page, index, pp. 1-6,54,132,233. (Year: 2019).*

* cited by examiner

*Primary Examiner* — June Hwu
(74) *Attorney, Agent, or Firm* — Penny J. Aguirre

(57) ABSTRACT

A new cultivar of *Rudbeckia* plant named 'RUDTI124' that is characterized by its short plant height, its well-branched plant habit, its very floriferous blooming habit, its long flowering period, and its ray florets that are grey-purple to brown on lower ⅔rd of the florets and yellow-orange on upper ⅓rd of the florets.

2 Drawing Sheets

Botanical classification: *Rudbeckia hirta.*
Variety denomination: 'RUDTI124'.

CROSS-REFERENCE TO A RELATED APPLICATION

This application is related to a European plant breeders' rights application filed on Sep. 5, 2018, application No. 2018/2289. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Rudbeckia hirta* and will hereafter by referred to by its cultivar name, 'RUDTI124'. The new cultivar is an herbaceous perennial grown for use as a landscape plant.

'RUDTI124' was derived from a breeding program in July of 2016 conducted by the Inventor at a nursery in Zuidwolde, The Netherlands. The objective of the breeding program was to select new cultivars of *Rudbeckia* with floriferous blooming habits and compact plant habits.

'RUDTI124' was selected in July of 2017 by the Inventor from amongst seedlings in a trial field that had been planted with seed derived from open pollination of numerous unpatented and unnamed proprietary plants from the Inventor's breeding program. The exact parentage is therefore unknown.

Asexual propagation of the new cultivar was first accomplished under the direction of the Inventor by tissue culture using meristematic tissue in Heerhugowaard, The Netherlands in January of 2018. Asexual propagation by tissue culture has determined that the characteristics of the new cultivar are stable and are reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure include but may not be limited to a website listing by AB-Cultivars (a company owned by the Inventor).

SUMMARY OF THE INVENTION

The following traits have been repeatedly observed and represent the characteristics of the new cultivar. These attributes in combination distinguish 'RUDTI124' as a unique cultivar of *Rudbeckia*.

1. 'RUDTI124' exhibits a short plant height.
2. 'RUDTI124' exhibits a well-branched plant habit.
3. 'RUDTI124' exhibits a very floriferous blooming habit.
4. 'RUDTI124' exhibits a long flowering period.
5. 'RUDTI124' exhibits inflorescences with ray florets that are grey-purple to brown on the lower ⅔rd of the florets and yellow-orange on the upper ⅓rd of the florets.

'RUDTI124' can be compared to the *Rudbeckia* cultivars SMILEYZ® 'Chocolate' (not patented), and SMILEYZ® 'RUDHT37' (U.S. Plant Pat. No. 30,657). SMILEYZ® 'Chocolate ' is similar to 'RUDTI124' in having strong stems. SMILEYZ® 'Chocolate' differs from 'RUDTI124' in having a taller plant height and ray florets that are dark grey-orange in color and not bicolored. 'RUDHT37' is similar to 'RUDTI124' in floriferous blooming habit. 'RUDHT37' differs from 'RUDTI124' in having a smaller disk diameter, in commencing bloom later blooming season, and in having ray florets colors that are clear grey-orange on the lower half and dark yellow-orange on the upper half.

BRIEF DESCRIPTION OF THE DRAWINGS

The accompanying colored photographs illustrate the overall appearance and distinct characteristics of the new *Rudbeckia*. The photographs were taken of a 4-month-old plant of 'RUDTI124' as grown outdoors in a 19-cm container in Zuidwolde, The Netherlands.

The photograph in FIG. 1 is a side view of 'RUDTI124' in bloom.

Figure 1:
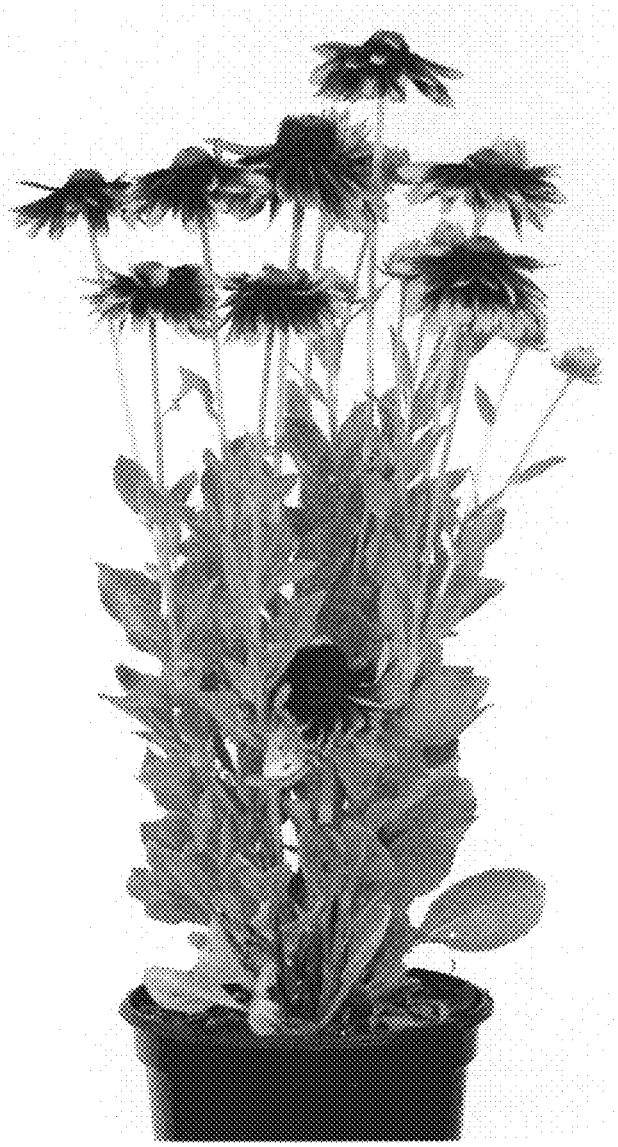
Figure 2:
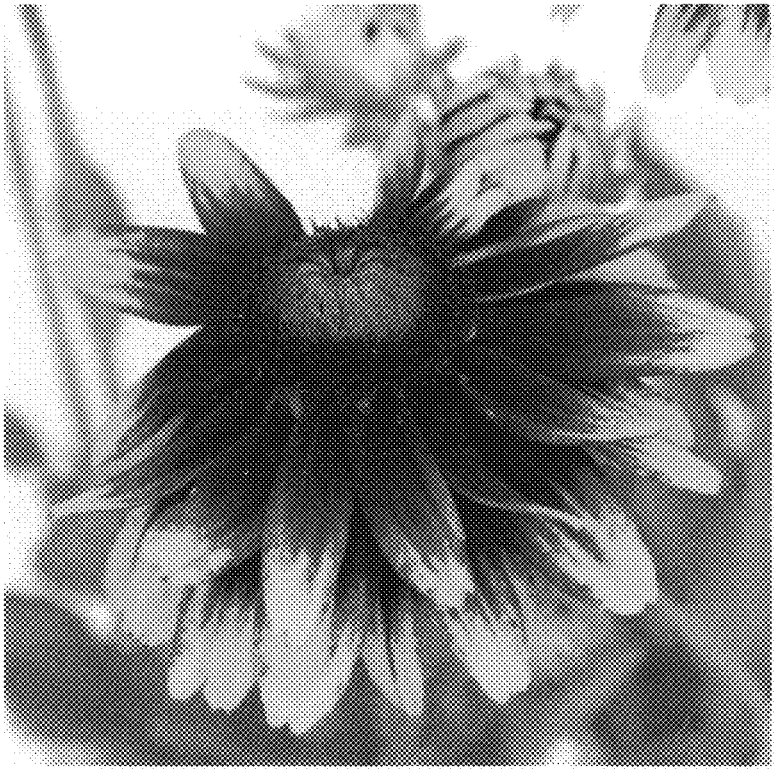

The photograph in FIG. 2 provides a close-up view of an inflorescence of 'RUDTI124'.

Figure 3:
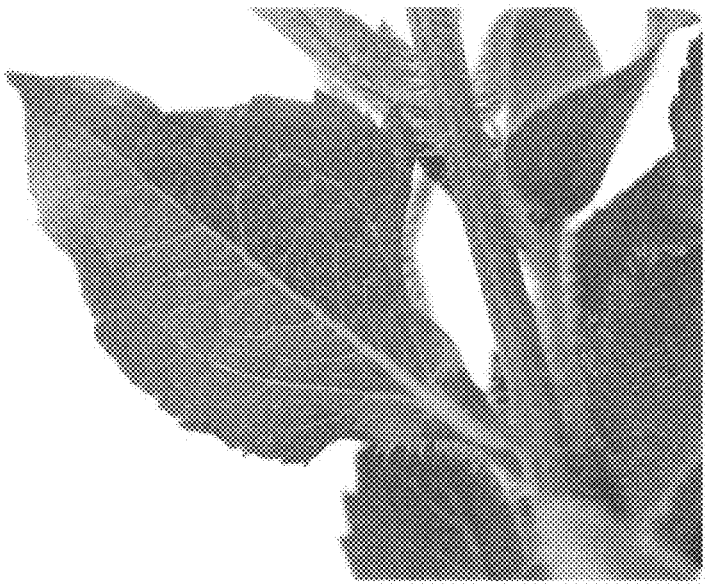

The photograph in FIG. 3 provides a close-up view of the foliage of 'RUDTI124'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 4-month-old plants of 'RUDTI124' as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Average of 13 weeks from early summer to late summer in The Netherlands.

*Plant type*.—Perennial.

*Plant habit*.—Broadly upright, compact.

*Plant shape*.—Narrow obovate.

*Height and spread*.—Average of 43 cm in height from soil level to top of foliar plane and 57.3 cm in height from soil level to top of floral plane, 30.8 cm in diameter.

*Hardiness*.—At least in U.S.D.A. Zones 4 to 10.

*Diseases and pests*.—No susceptibility or resistance to diseases or pests has been observed.

*Root description*.—Fine and fibrous.

*Propagation*.—Tissue culture.

*Root development*.—An average of 3 weeks for root initiation with a young rooted plant produced in an average of 6 weeks.

*Growth rate and vigor*.—Vigorous.

Stem description:

*Shape*.—Moderately angled.

*Stem color*.—Young stems; 144B, internodes; 144B, angles 144A, mature stems; 144B, tinged 187B to 187C.

*Stem size*.—An average of 4.5 mm in diameter and an average of 26 cm in height.

*Stem surface*.—Moderately glossy and densely covered with strigose hairs; an average of 2 mm in length and close to NN155D in color.

*Stem number*.—Average of 13 main stems, 1 lateral branch per main stem.

*Internode length*.—An average of 2.7 cm in length.

*Stem aspect*.—Main stems; average of 10° to vertical, lateral branches; average of 20° to main stems.

*Branching*.—Freely branching from base with lateral stems.

Foliage description (cauline leaves):

*Leaf shape*.—Elliptic to obovate.

*Leaf division*.—Simple.

*Leaf base*.—Cuneate.

*Leaf apex*.—Acute.

*Leaf venation*.—Pinnate, color upper surface 145C, color lower surface 145A.

*Leaf margins*.—Coarsely serrate, coarsely slightly undulate.

*Leaf attachment*.—Petiolate.

*Leaf arrangement*.—Alternate.

*Leaf size*.—Average of 6.8 cm in length and 3.9 cm in width.

*Leaf color*.—Young upper surface; 143B, young lower surface; 144B and 146C, mature upper surface; 143A, mature lower surface; 143B and 144B.

*Leaf surface*.—Both surfaces rough to the touch, matte and densely pubescent with short strigose hairs; an average of 2 mm in length and NN155D in color.

*Petioles*.—Average of 2.5 cm in length, flattened, average diameter at widest point 7 mm and at narrowest point 3 mm, upper surface color; 145D, margins 143B, lower surface color; 144A, margins 144A, both surfaces slightly glossy and densely covered with strigose hairs; an average of 2 mm in length and NN155D in color.

Foliage description (basal leaves): All characteristics match cauline leaves with the following characteristics differing: Arrangement; emerging from base, leaf size: 9.5 cm in length and 4.5 cm in width, leaf shape; obovate.

Flower description:

*Type*.—Terminal capitulum, consisting of ray florets and disk florets.

*Capitulum number*.—1 per stem, up to 20 per plant.

*Lastingness of inflorescence*.—Average of 2 weeks, persistent.

*Capitulum size*.—Matures to about 4.9 cm in height and 10.2 cm in diameter, disk is an average of 3.2 cm in diameter.

*Fragrance*.—None.

*Involucral bracts (phyllaries)*.—Broadly cuneate base, obtuse to bluntly acute apex, narrow oblong in shape, entire margins, average of 36 arranged in 2 rows, rotate in arrangement, held in an average of −45°, 1.6 cm in length and 4 mm in width, color; upper surface when fully open 143B, lower surface when fully open 144A and 144B, both surfaces matte and densely covered with strigose hairs; an average of 2 mm in length and NN155D in color.

*Receptacle*.—Near orbicular in shape, an average of 7 mm in height and diameter, 157A and 157B in color.

*Buds*.—Globular in shape, immature ray florets pointed upward and curling inward, up to 2.1 cm in length and 3.8 cm in diameter, immature ray florets 151D in color, immature involucral bracts upper surface 143A in color, immature involucral bracts lower surface 143C in color, surface on involucral bracts and immature ray florets is matte and densely covered with strigose hairs; an average of 2 mm in length and NN155D in color with hairs adpressed on immature ray florets.

*Peduncle*.—Strong, straight on top of main flowering stem, average of 19.3 cm in length and 4 mm in diameter, color; 144B and axially striped 143B, surface moderately glossy and densely covered with short strigose hairs; an average of 2 mm in length and NN155D in color.

*Ray florets*.—Average of 29 (varying between 26 and 35), rotate around the disk, oblong in shape, average of 4.8 cm in length and 1.8 cm in width, praemorse apex, cuneate base, entire margins, both surfaces are velvety, matte and glabrous, densely covered with very short strigose hairs, 0.5 mm in length and 200C in color, held in a −40° angle, color: when opening upper side; lower half a color between N186C and 200A, upper half a color between 14A and 17B, when opening lower side; upper half 13B, lower half 151A, when fully open upper and lower side; lower ⅔rd a color between N186C and 200A, upper ⅓rd 17B, when fully open lower side; upper half 13B, lower half 151A, veins 144A and 144B.

*Disk flowers*.—Average about 600 slightly curved and tubular in shape, 16 whorls arranged spirally on a conical receptacle, lower 90% fused into tube, upper 10% free, tubular, about 8.5 mm in length and 4 mm in width, free lobes have entire margins, apices of free lobes acute and curled backwards, both surfaces glabrous and slightly glossy, color; when opening and fully open upper and lower surface 203A, mid-section 200A, base 155A, spines; none, bracts; 1 per disk floret, an average of 6 mm in length and 1.5 mm in diameter, oblanceolate in shape, acute apex, narrowly cuneate base, color; apex 187A, mid-section 157A, margined 187A, base 157A, surface matte and moderately pubescent with hairs; an average of 0.3 mm in length, 187D in color.

Reproductive organs:

*Gynoecium*.—Pistil; 1, 8 mm in length, style; 5 mm in length, color; top 200A, mid-section 155C, tinged 187C, base 155C, stigma; cleft, decurrent, 4 mm in diameter, 200A in color, ovary; 155A in color.

*Androecium*.—Stamens; 5, filaments; 2 mm in length, 157A in color, anther; narrow oblong in shape, 3 mm in length, 0.5 mm in width, 200A in color, pollen; moderate in quantity and 15A in color.

*Fruit/seed*.—None observed to date.

It is claimed:

1. A new and distinct cultivar of *Rudbeckia* plant named 'RUDTI124' substantially as herein illustrated and described.

* * * * *